(12) United States Patent
Merritt et al.

(10) Patent No.: US 9,506,487 B1
(45) Date of Patent: Nov. 29, 2016

(54) CLAMP MECHANISM FOR USE WITH A SHORT POLE WHICH RETAINS IV BAGS AND MOTORIZED MEDICINE DISPENSING MACHINES

(71) Applicants: Dennis L. Merritt, Simi Valley, CA (US); Charles Allen Cordy, San Marcos, CA (US)

(72) Inventors: Dennis L. Merritt, Simi Valley, CA (US); Charles Allen Cordy, San Marcos, CA (US)

( * ) Notice: Subject to any disclaimer, the term of this patent is extended or adjusted under 35 U.S.C. 154(b) by 0 days.

(21) Appl. No.: 14/738,701

(22) Filed: Jun. 12, 2015

(51) Int. Cl.
*A47F 5/00* (2006.01)
*F16B 7/04* (2006.01)
*F16B 2/06* (2006.01)
*F16M 13/02* (2006.01)
*A61M 5/14* (2006.01)

(52) U.S. Cl.
CPC .......... *F16B 7/0433* (2013.01); *A61M 5/1415* (2013.01); *F16B 2/065* (2013.01); *F16M 13/022* (2013.01)

(58) Field of Classification Search
CPC ... F16B 7/0433; F16B 2/065; F16M 13/022; A61M 5/1415
USPC .............. 248/229.25, 229.15, 230.6, 231.71, 248/125.7; 211/74
See application file for complete search history.

(56) References Cited

U.S. PATENT DOCUMENTS

| | | | |
|---|---|---|---|
| 2,970,798 A * | 2/1961 | Friotchle | B01L 9/50 24/335 |
| 3,709,372 A | 1/1973 | Alexander | |
| 5,174,533 A | 12/1992 | Pryor et al. | |
| 5,421,548 A * | 6/1995 | Bennett | A61G 5/10 248/129 |
| D364,555 S | 11/1995 | Neiert | |
| D370,061 S | 5/1996 | Shirley | |
| 6,079,678 A | 6/2000 | Schott et al. | |
| 6,585,207 B2 | 7/2003 | Ibbitson et al. | |
| 7,182,032 B1 | 2/2007 | Lindemann | |
| 7,676,865 B2 * | 3/2010 | Graham | A61G 7/0503 248/158 |
| 8,141,839 B2 | 3/2012 | Buchner | |
| 8,459,602 B2 | 6/2013 | Herskovic | |
| 2007/0069093 A1 * | 3/2007 | Graham | A47B 81/061 248/231.71 |
| 2009/0050756 A1 * | 2/2009 | Newkirk | A61G 7/0503 248/176.1 |
| 2009/0314923 A1 * | 12/2009 | Timoszyk | A61G 12/004 248/647 |

* cited by examiner

*Primary Examiner* — Gwendolyn Baxter
(74) *Attorney, Agent, or Firm* — Thomas I. Rozsa

(57) ABSTRACT

An attaching clamping mechanism which is clamped onto an existing pole of a hospital bed and retains the unsupported short pole adjacent the hospital bed. Through the clamp apparatus the short pole is used to retain sterile bags of medicine with fluid transportation lines which are connected to the sterile bag at one end and at the opposite end may be directly connected to a needle inserted into a patient for intravenous administration of medicine or alternatively connected to a motorized dispensing machine which regulates the dosage of medicine and period of time for intravenous medicine administration with a separate fluid transportation line extending from the dispensing machine to a needle inserted into a patient. The short pole is only between twenty-four (24) inches and thirty-six (36) inches.

7 Claims, 9 Drawing Sheets

CLAMP MECHANISM FOR USE WITH A SHORT POLE WHICH RETAINS IV BAGS AND MOTORIZED MEDICINE DISPENSING MACHINES

BACKGROUND OF THE INVENTION

1. Field of the Invention

The present invention relates to the field of support poles which are used to retain sterile bags of medicine with fluid transportation lines which are connected to the sterile bag at one end and at the opposite end may be directly connected to a needle inserted into a patient for intravenous administration of medicine or alternatively connected to a motorized dispensing machine which regulates the dosage of medicine and period of time for intravenous medicine administration with a separate fluid transportation line extending from the dispensing machine to a needle inserted into a patient.

The support poles in the field of the present invention involves intravenous administration of medicine to a patient in a hospital, a medical care facility, nursing homes, and other location where a patient is usually in a hospital bed and receives intravenous medication.

2. Description of the Prior Art

The following nine patents are the closest prior art known to the inventors.

1. U.S. Pat. No. 3,709,372 issued to Larry T. Alexander on Jan. 9, 1973 for "Intravenous Supply Container Support" (hereafter the "Alexander Patent");

2. U.S. Pat. No. 5,174,533 issued to Jeffrey W. Pryor et al. Dec. 29, 1992 for "Adjustable Instrument Mounting Assembly" (hereafter the "Pryor Patent");

3. U.S. Pat. No. Des. 364,555 issued to Todd W. Neiert on Nov. 28, 1995 for "Intravenous Bottle Stand Clamp" (hereafter the "Neiert Design Patent");

4. U.S. Pat. No. Des. 370,061 issued to Terry L. Shirley on May 21, 1996 for "I.V. Pole Clamp" (hereafter the "Shirley Design Patent");

5. U.S. Pat. No. 6,079,678 issued to Jeffrey C. Schott et al. on Jun. 27, 2000 for "Intravenous Stand Support Assembly" (hereafter the "Schott Patent");

6. U.S. Pat. No. 6,585,207 issued to Scott Alan Ibbitson et al. on Jul. 1, 2003 for "Safety Clamp Holder" (hereafter the "Ibbitson Patent");

7. U.S. Pat. No. 7,182,032 issued to David C. Lindemann on Feb. 27, 2007 for "Clamp Tool Device and Method fo Using" (hereafter the "Lindemann Patent");

8. U.S. Pat. No. 8,141,839 issued to Michael R. Buchner on Mar. 27, 2012 for "Pole Mounting Device" (hereafter the "Buchner Patent");

9. U.S. Pat. No. 8,459,602 issued to Arnold Herskovic on Jun. 11, 2013 for "Clamping Device" (hereafter the "Herskovic Patent").

The Alexander Patent discloses a standard pole which is affixed to a bed and then a cross bar which is affixed to the pole. This is described in detail in FIGS. 4 and 5 and discussed in Column 2 Lines 30 through 67 of the patent text.

The Pryor Patent discloses: an adjustable mounting assembly for mounting an instrument on a support member having a first clamping device for releasable clamping engagement with the support member and a second clamping device for securing to an instrument or piece of equipment, with a lockable, adjustable connection between the two clamping devices allowing adjustment about two perpendicular axes to allow the instrument orientation to be adjusted."

The Neiert Design Patent discloses a design patent for an intravenous bottle stand clamp.

The Shirley Design Patent discloses a single clamping mechanism.

The Schott Patent discloses a pole affixed to a bed post by the double arcuate members.

The Ibbitson Patent discloses: an adjustable clamp holder having multiple securing mechanisms for each attachment structure of the clamp body. The clamp has utility in fastening together support rods and supporting an apparatus or laboratory equipment.

The Lindemann Patent discloses a clamp tool for use in holding a boat in a relatively stationary position while the boat is floating in shallow water.

The Buchner Patent discloses a mounting device for a pole comprising: a holder portion having an open first end, a spaced, open second end, an interior surface and an exterior surface, said interior surface being shaped at said first end to define a pole cavity sized to receive an end of said pole, said interior surface of said holder portion being shaped to define a ball socket spaced in from said second end of said holder portion, a support portion having an elongated rod with a first end and a spaced second end, and a ball on said first end of said rod, said ball being sized to fit into said ball socket to form a ball joint with said ball socket with said rod extending transverse to said holder portion and said holder portion being rotatable relative to said rod about a first axis and about a second axis transverse to said first axis, and means, connected to said second end of said rod, for removably attaching said support portion to a structure, whereby said pole is positioned by rotation of said holder portion about said first and second axes.

The Herskovic Patent discloses a clamping device for attaching a piece of first moveable equipment to a piece of second moveable equipment comprising a body, a mounting portion, and an attachment portion. The attachment portion comprises an attachment recess disposed within the body for receiving the piece of first movable equipment, and a latch plate rotatably attached to the body at a pivot disposed on one side of said attachment recess, wherein the latch plate may be pivotally disposed between an open position and a closed position. The latch plate further having an attachment lock disposed within the latch plate.

None of the prior art references addresses the problems identified by the present inventors. The problems are in general that in the hospital setting, most hospital beds have at least one extended pole into which there is a clamp which connects a long pole that has the various IV medications attached to the pole in almost a circular configuration or in a multiplicity of extending configurations wherein there is one IV bag per pole and the bag has a tube coming from it and each respective tube is then connected to a motorized dispensing apparatus which dispenses the medication from the particular bag into an IV needle that dispenses specific quantities of medication to the patient at specific times. If the patient needs to be transported from one location to another such as from the hospital bed to another hospital facility within the hospital such as a CAT scan, an MRI, etc. or if the patient needs to be transferred from one room to another, the standard practice is to have the long pole which has wheels on it and has the heavy IV medication and motorized dispensing machines thereon moved by one attendant while another attendant pushes the patient's bed and a third attendant follows to be sure that no lines become disconnected as the patient is being transported from one location to another.

Other problems associated with the use of a long pole is that hospital elevators are long but usually not wide and the additional width created by the long pole adjacent the bed makes it more difficult to use an elevator to transport a patient from one location to another.

There is a significant need to address these problems.

SUMMARY OF THE INVENTION

One of the co-inventors, Dennis Merritt, is an interventional radiology technician with many years of experience in administering intravenous medications to hospital patients. He has identified the shortcomings set forth in the previous sections of this patent application.

A short pole (also being an unsupported pole since it is not on a base and cannot stand alone) is a pole that exists in hospitals but is almost never used. Throughout this patent application including the claims, the term "short pole" means "an unsupported pole". The existing short pole has a multiplicity of retaining members which can be used to retain sterile bags of medicine with fluid transportation lines which are connected to the sterile bag at one end and at the opposite end may be directly connected to a needle inserted into a patient for intravenous administration of medicine or alternatively connected to a motorized dispensing machine which regulates the dosage of medicine and period of time for intravenous medicine administration with a separate fluid transportation line extending from the dispensing machine to a needle inserted into a patient. The short pole is only between twenty-four (24) and thirty-six (36) inches long and does not have any base or rolling wheels. It in theory could be placed in a support receiving opening in a hospital bed, but in general, since hospital beds usually don't have such supporting openings, the short pole is not used.

The present invention is an attaching clamping mechanism which is clamped onto an existing pole of a hospital bed and retains the short pole adjacent the hospital bed. Through the present invention clamp apparatus, the short pole is used to retain sterile bags of medicine with fluid transportation lines which are connected to the sterile bag at one end and at the opposite end may be directly connected to a needle inserted into a patient for intravenous administration of medicine or alternatively connected to a motorized dispensing machine which regulates the dosage of medicine and period of time for intravenous medicine administration with a separate fluid transportation line extending from the dispensing machine to a needle inserted into a patient. The short pole is only between twenty-four (24) inches and thirty-six (36) inches.

The present invention clamp apparatus is attached to a bed rail or a vertical pole on the bed so the clamp apparatus enables the short pole to be retained in an operative condition adjacent the bed.

With the short pole retained adjacent the bed, if the patient needs to be transported from one location to another such as from the hospital bed to another hospital facility within the hospital such as a CAT scan, an MRI, etc. or if the patient needs to be transferred from one room to another, the short pole is moved with the hospital bed, one attendant is needed to move the bed. The necessity of the second attendant to move a long pole with the medications thereon and the third attendant to follow to make sure the medication lines do not become entangled is eliminated.

With the present invention, instead of being clamped to a long pole, it is clamped to a patient's bed. In the present invention a short cylinder in the clamping apparatus is designed to accommodate a short pole which is only about 2 to 3 feet tall and contains all the heavy medications in separate bags in separate transverse rods that extend from the short pole with a vertical portion to prevent the bag from falling out. The bag typically has a hole which is extended through the transverse portion and then retained on the horizontal portion of the rod affixed to the pole and then there is a fluid dispensing tube that goes from the bag to the heavy motor and from the heavy motor into an IV needle which goes into the patient. The short pole is affixed within a cylinder of the present invention clamp by a threaded bolt affixed to a knob, with the threaded bolt retaining the short pole within the cylinder of the clamp.

A key innovation of the present invention clamp is the distance created between the location of where the pole on the hospital bed is located and where the short pole retained by the present invention clamp is located. The short pole, even without the medication bags and dispensing motor is heavy. The present invention clamp apparatus is first clamped to the pole of the hospital bed. A person's hand is required to grasp the short pole and insert it into the opening of the receiving and retaining member of the present invention clamp. The present invention clamp has a given distance between the location of the clamped bed pole and the short pole receiving and retaining member to enable a person's hand grasping the short pole to fit between the clamped bed pole and the short pole as the short pole is inserted into the present invention clamp receiving and retaining member which by way of example is a cylinder with a cylindrical opening to receive the short pole which is usually cylindrical. This given distance is between the range of ⅜ inches and 6 inches to accommodate different sized fisted hands.

Clamps in existence do not have this distance in the clamp design. An innovation of the present invention is the extra distance between the cylindrical opening of the clamp receiving and retaining member and the clamped bed pole so that a person's hand can get into that location and then the entire device is in one compact unit on the bed so the patient can be easily transported from one location to another. If the short pole is at an adjacent location on a table adjacent the patient's bed, it can easily be lifted up and put into the cylindrical opening of the present invention and clamped tight so that the short pole now can be affixed to the bed and can be transported in one operation where only one person is needed.

Other hospital items such as a wheelchair also have poles to which the present invention clamp is attached. The short pole with the medication and dispensing mechanism attached is removed from the present invention clamped to the hospital bed into the receiving and retaining member of the present invention clamp retained on a pole of the wheelchair.

It is an object of the present invention to provide a clamp having a given distance created between the location of where the pole on the hospital bed is located and where the short pole retained by the present invention is clamped located. The short pole, even without the medication bags and dispensing motor is heavy. The present invention clamp apparatus is first clamped to the pole of the hospital bed. A person's hand is required to grasp the short pole and insert it into the opening of the receiving and retaining member of the present invention clamp. It is an object of the present invention clamp to have a given distance between the location of the clamped bed pole and the short pole receiving and retaining member to enable a person's fisted hand grasping the short pole to enable a fisted hand grasping the short pole to fit between the clamped bed pole and the short pole as the short pole is inserted into the present invention clamp receiving and retaining member. This given distance is between the range of ⅜ inches and 6 inches to accommodate different sized fisted hands.

A patient may need to use a wheelchair to go to the bathroom. Other hospital items such as a wheelchair also have poles to which the present invention clamp is attached. A separate second clamp of the present invention is clamped to the pole of the wheelchair It is a further object of the present invention to provide two separate present invention clamps so that the short pole with the medication bags and heavy dispensing machine is transferred from the present invention clamp attached to a hospital bed to the present invention clamp attached to a wheelchair pole.

It a further object of there sent invention to have a multiplicity of present invention clamps affixed to different poles on objects selected from the group consisting of hospital beds, wheelchairs, examination tables, and any object where a short pole with medication and dispensing apparatus is required to be positioned adjacent a person requiring infusion medication.

It is an additional object of the present invention to provide improvements to the short pole. Existing short poles have a straight bottom surface making it difficult to align the bottom of the pole with the opening in the present invention clamp cylindrical receiving member. An improvement in the short pole is to taper the bottom end so that insertion into the opening of the clamp receiving member is easier to perform.

IV bag retaining poles, whether long poles with wheels or short poles have their hanger bars positioned at 90 degrees to each other. With this orientation, it creates a problem of a hanger bar of one pole becoming entangled with a hanger bars of another pole. It is an additional object of the present invention to include having a notched interface at the location where the two hanger bars intersect, to enable the angle between hanger bars to be reduced from 90 degrees to between a range of 45 degrees and 60 degrees Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF EMBODIMENTS OF THE PRESENT INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
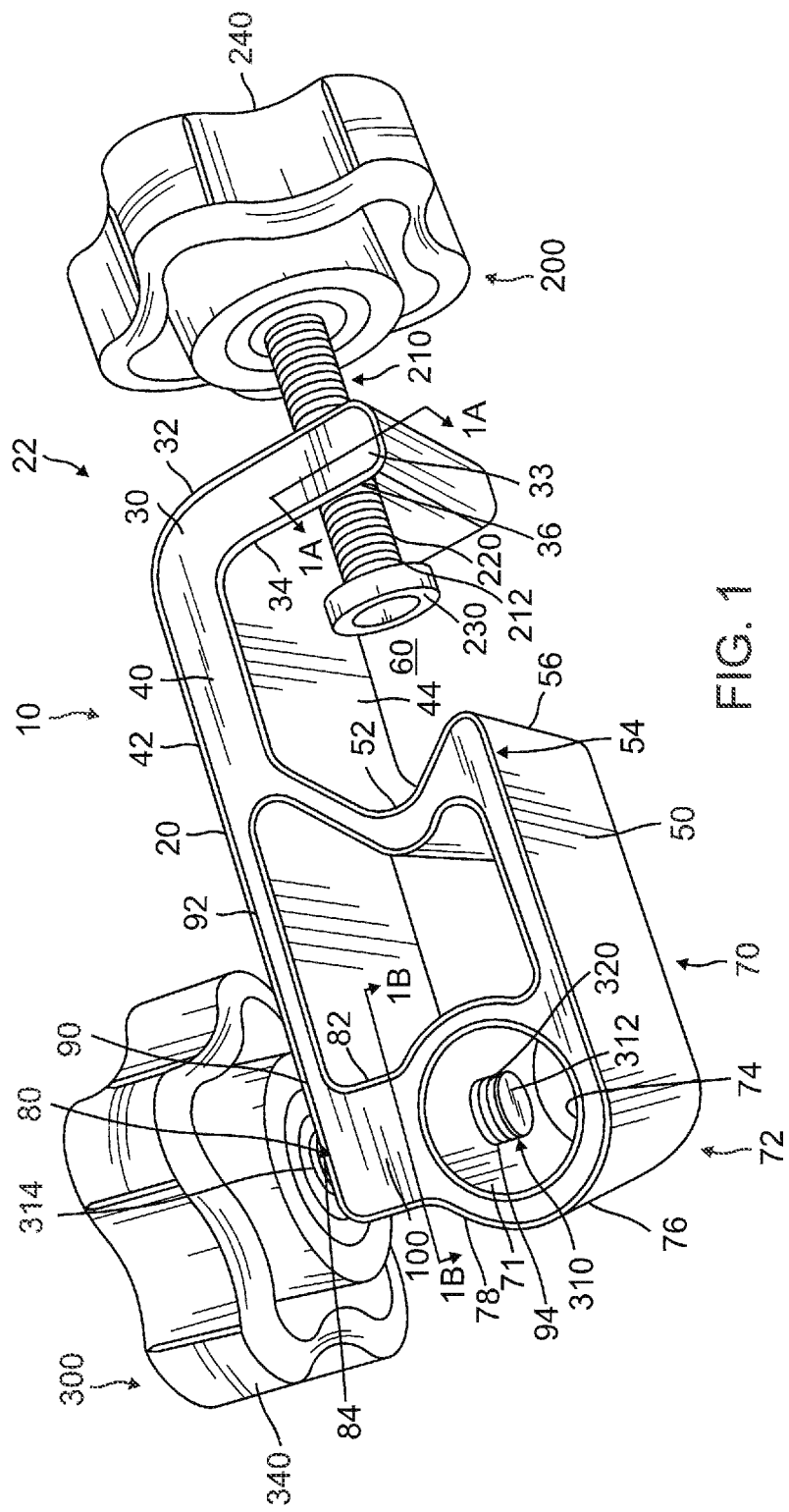
FIG. 1 is a top perspective view of the present invention clamp apparatus.
Figure 2:
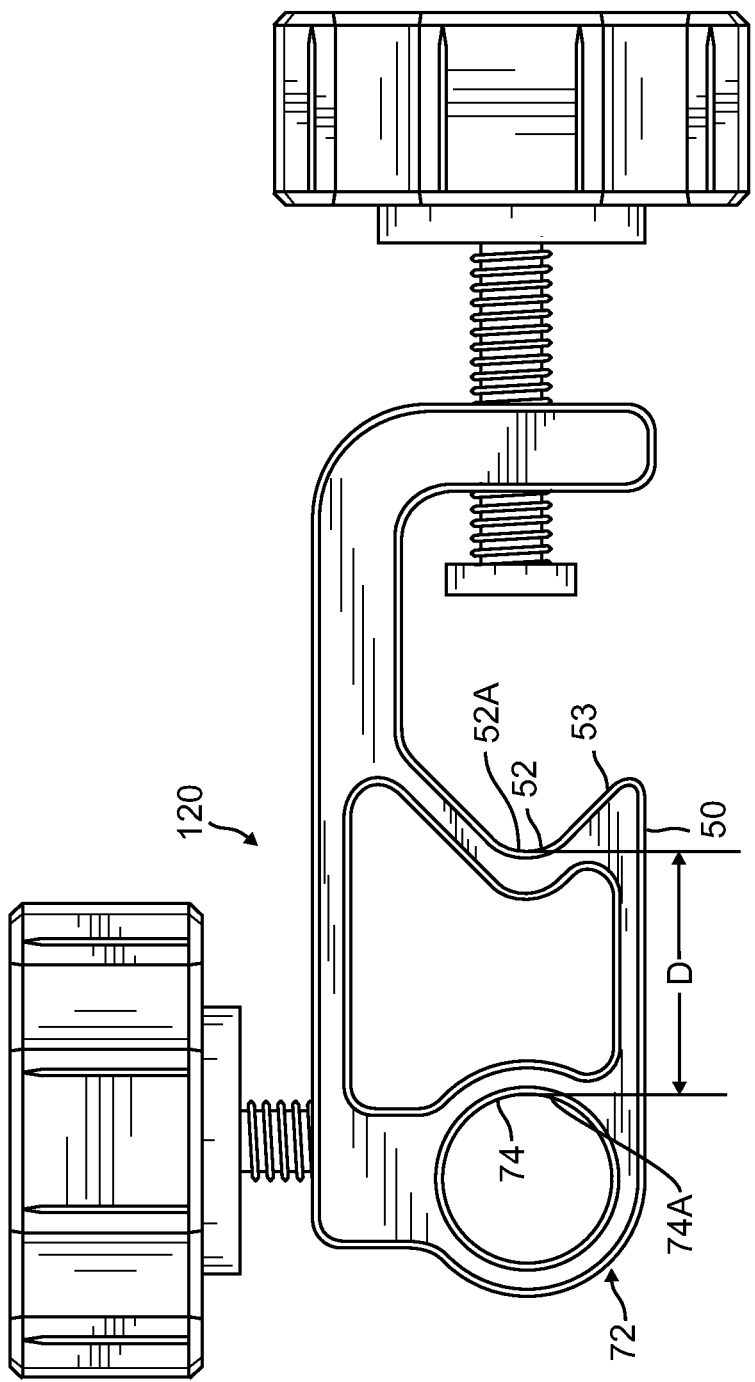
FIG. 2 is a top plan view of the present invention clamp apparatus.
Figure 3:
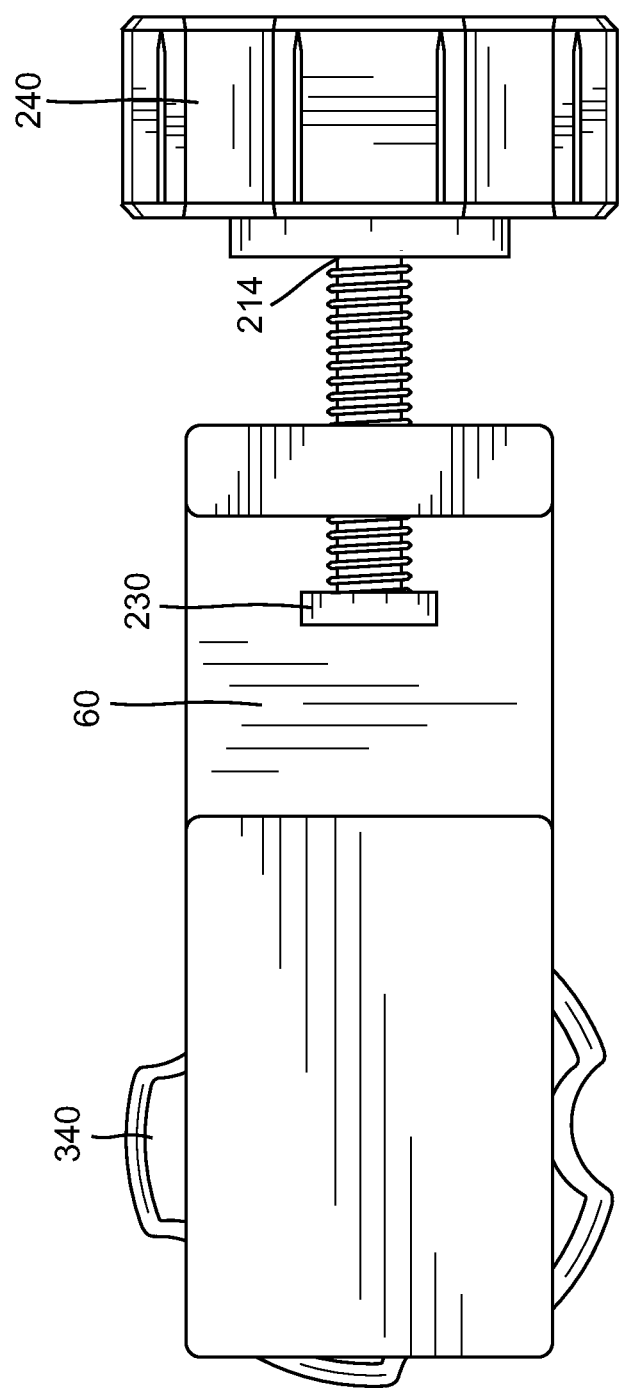
FIG. 3 is a bottom plan view of the present invention clamp apparatus.

Referring to FIGS. 1, 2 and 3, there are respectively illustrated a perspective view, a top plan view and a bottom plan view of the present invention clamping apparatus 10. The body 20 of the clamping apparatus 10 is one integral unit with two separate threaded rods respectively affixed to a turning knob as will be described.

Figure 1A:
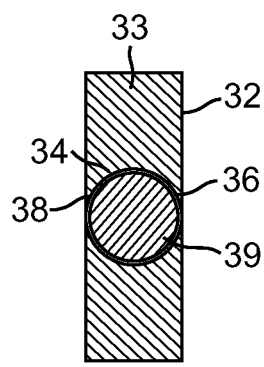
FIG. 1A is a cross-sectional view taken along line 1A-1A of FIG. 1.

The body 20 of the clamping apparatus 10 has a first spacer section 22 including a bent sidewall section 30 and a longitudinal section 40. Referring to FIGS. 1 and 1A, the bent sidewall section 30 extends from an outer surface 32 through wall 33 to an inner surface 34 with an interior opening 36 have a threaded sidewall 38 with threads 39 which extend from outer surface 32 to inner surface 34. A first affixation member 200 includes a rod 210 with threads 220 threadedly extending through opening 36 and engaged with threads 39. A retaining plate 230 is affixed at a proximal end 212 of rod 210 and a closing knob 240 is affixed at distal end 214 of rod 210.

The longitudinal section 40 has an outer surface 42, a body 43, and an inner surface 44. The first spacer section 22 terminates in an interior wall 50 extending from inner surface 44 of longitudinal section 40. The interior wall 50 has a concave cavity 52 aligned with retaining plate 230. Interior wall 50 has a distal longitudinal section 54 terminating in a free end 56.

An object such as a integral pole 500 (See FIG. 7) of a hospital bed or wheelchair extends through a first clamp opening 60 and is retained within clamp 10 by a press fit retention created by rotation of closing knob 240 to cause retaining plate 230 to press against integral pole 500 so that the integral pole 500 is press fit retained within concave cavity 56.

The present invention clamp 20 has a second section 70 which includes a cylindrical chamber 72 having an interior opening 71, an inner cylindrical surface 74 and an exterior cylindrical surface 76. A distal portion 78 of cylindrical surface 76 extends to a second spacer section 80 which is integral with cylindrical chamber 72. The second section includes a transverse spacer section 80 extending from proximal portion 82 of cylindrical surface 76 to a second longitudinal wall 90 which extends to a first longitudinal spacer wall 92 which is integral with longitudinal wall 40 of first spacer section 22.

Figure 1B:
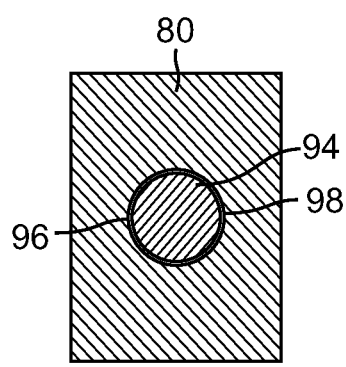
FIG. 1B is a cross-sectional view taken along line 1B-1B of FIG. 1.

Referring to FIGS. 1 and 1B, an interior opening 94 having a sidewall 96 with threads 98 which extend from an outer surface 84 of transverse spacer section 80 to cylindrical inner surface 74. A second affixation member 300 includes a rod 310 with threads 320 threadedly extending through opening 94 and engaged with threads 98. A closing knob 340 is affixed at distal end 314 of rod 310.

The short pole or unsupported pole 700 is inserted into interior opening 71 of cylindrical chamber 72 and is retained within interior opening 71 of cylindrical chamber 72 and is press fit retained within opening 71 of cylindrical chamber 72 by rotation of closing knob 340 to cause interior end 312 of rod 310 to press against the short pole or unsupported pole 700 so that the short pole is press fit retained within cylindrical chamber 72.

Figure 4:
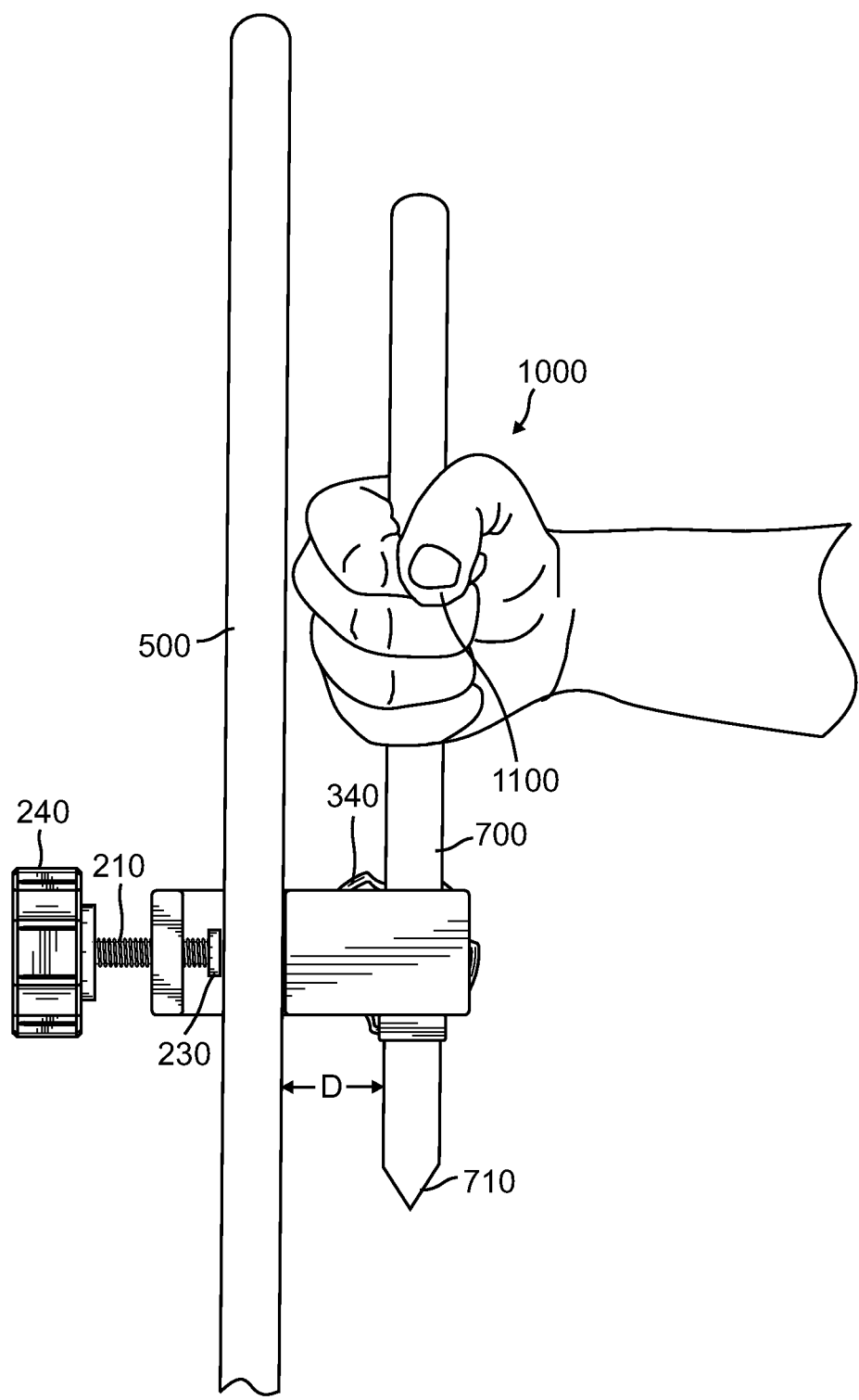
FIG. 4 is a side view illustrating a hand in a fisted condition holding onto a short pole after the short pole has been inserted into the receiving and retaining member of the present invention clamp apparatus and showing a portion of a pole which is part of a hospital bed or wheelchair with the present invention clamp apparatus clamped to that pole, also illustrating a present invention improvement in creating a tapered lower end to the short pole.

A key innovation of the present invention is the third spacer section 120 (also called an intermediate spacer member or intermediate spacer section) of the present invention clamp 10. The third spacer section 120 is formed between first section 20 and second section 70. The important distance "D" is referred to as an intermediate spacer distance and extends from the interior surface 52A of concave cavity 52 of interior wall 50 which is designated as clamp point one and numbered 52A, and the interior surface 74 of cylindrical chamber 72 at a location directly in line with clamp point one and which is designated as clamp point two and numbered 74A (see FIG. 2). This intermediate spacer distance "D" represents the distance between the short pole 700 and the extending pole 500. Referring to FIG. 4, there is illustrated a hand 1000 grasping the short pole 700 just as it is inserted into opening 71 of cylindrical member 72 illustrating that the present invention clamp 10 is configured to provide a spacer distance "D" to enable a first 1100 of a person 1000 grasping the short pole 700 and not having the hand 1000 hit or rub against the extending pole 500. The third spacer section 120 facilitates the spacer distance "D" which is sized to be from ⅜ inches to 6 inches accommodated different sized hands and which enables a fisted hand to be inserted between point one and point two.

Figure 5:
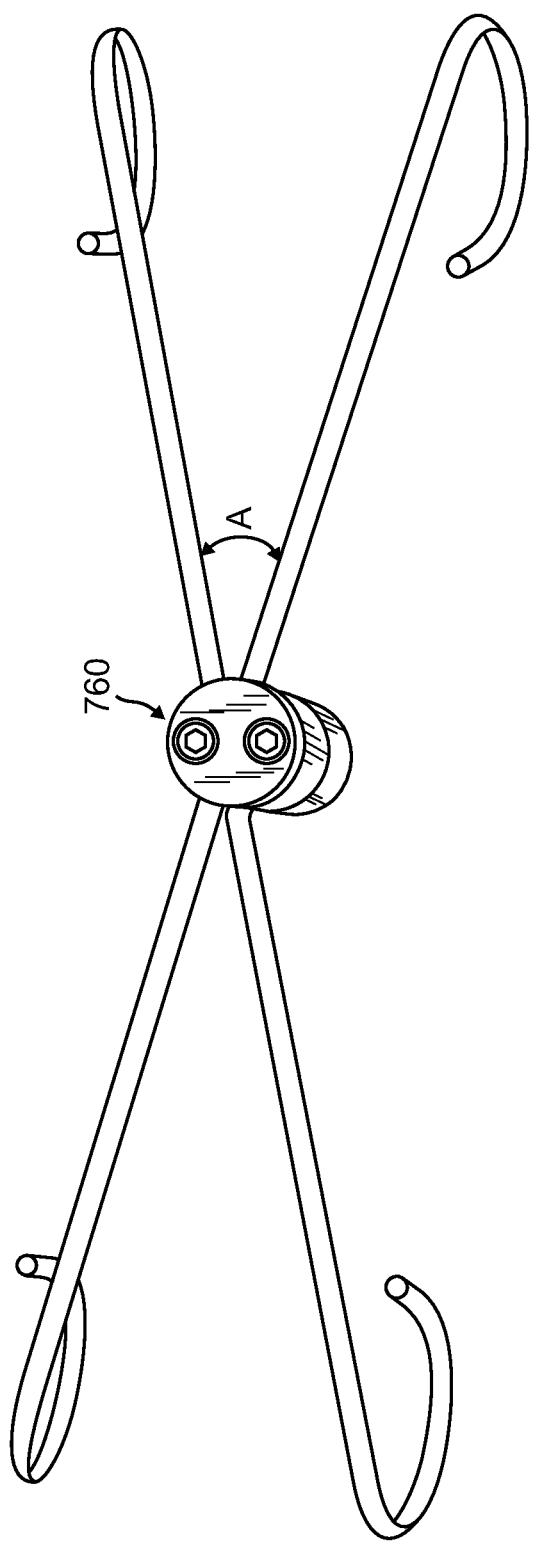
FIG. 5 is a perspective view of a top of an IV pole with the present invention hanger bar orientation with the hanger bars at an angle less than 90 degrees to each other.
Figure 6:
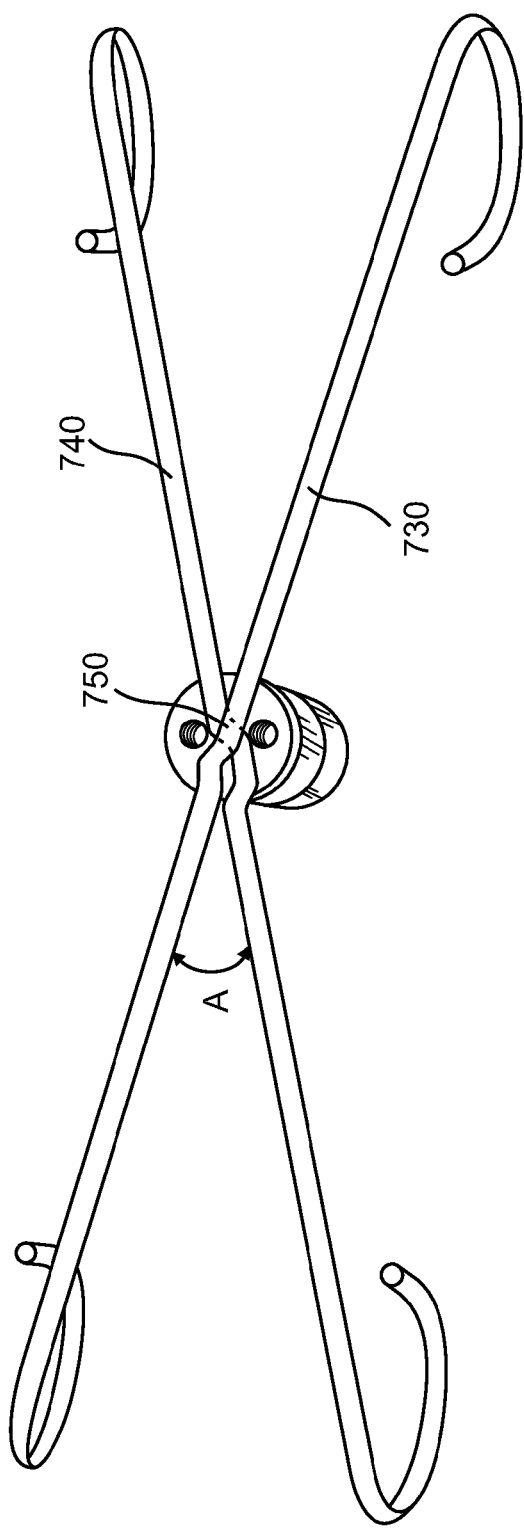
FIG. 6 is a cross-sectional view taken along line 6-6 of FIG. 7.

Two other improvements are also incorporated into the short pole 700. As illustrated inn FIG. 4, the bottom end 710 is tapered to facilitate insertion of the short pole 700 into the opening 71 of cylindrical member 72. Referring to FIGS. 5 and 6, the short pole 700 is also modified to create a notch 750 where hanger bar 730 and hanger bar 740 intersection within top cap 760, As a result, the angle "A" between hanger bars is reduced between 20 degrees and 60 degrees.

The short pole or unsupported pole 700 is illustrated as a single piece. In some applications, the short pole has a telescoping member wherein one section telescopes into the other to increase the overall height of the short pole. However, this portion of the short pole is in existence in the prior art and therefore, has not been illustrated with having a member that enables the short pole to be telescoping. However, it will be appreciated that the short pole can either be a single piece as illustrated or can be telescoping to increase the height or length of the short pole 700.

The present invention clamp 10 can be made of material selected from the group consisting of aluminum, steel and stainless steel.

Figure 7:
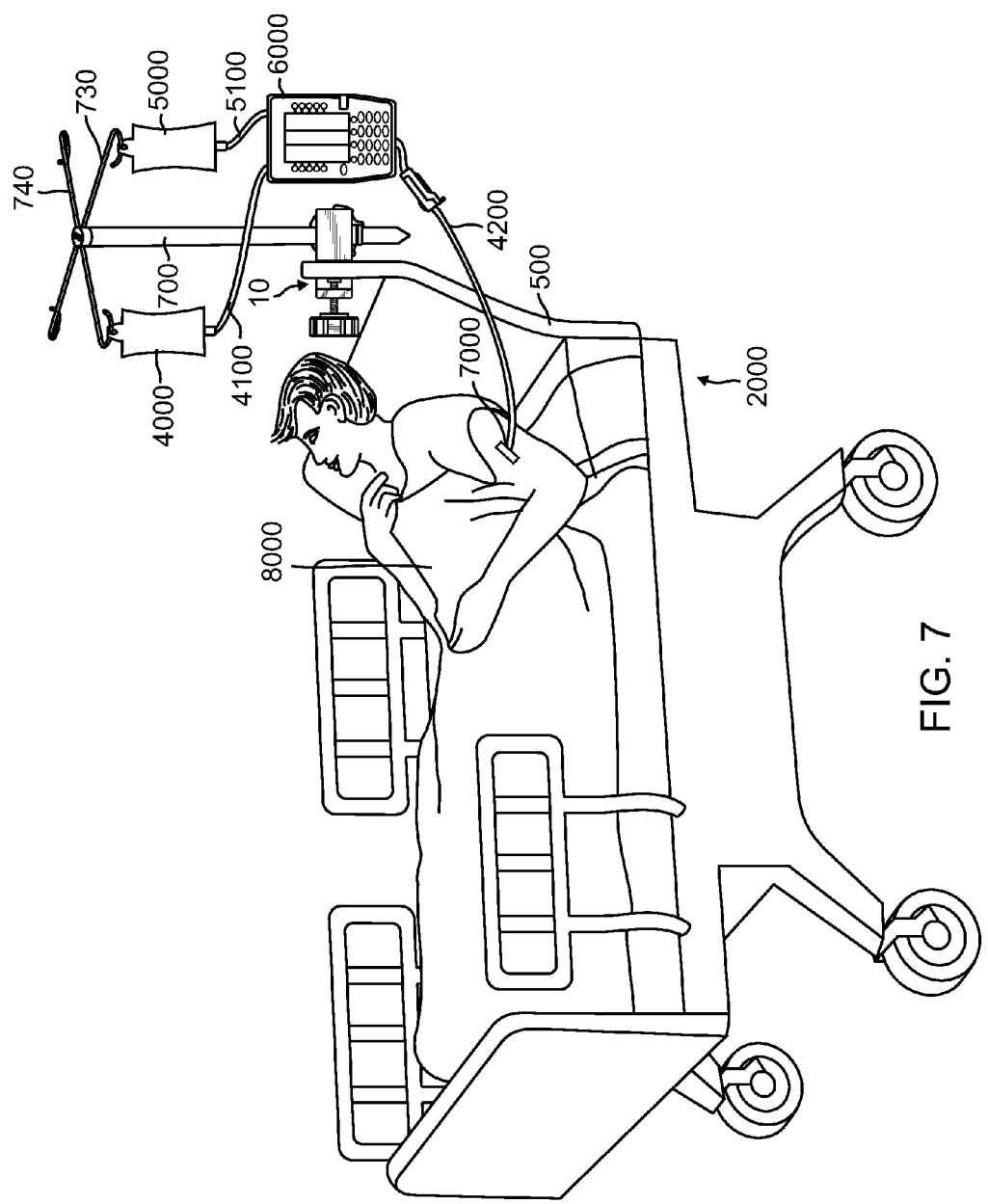
FIG. 7 is a perspective view of the present invention clamp apparatus clamped to pole of a hospital bed and retaining a short pole with IV medication bags retained on hanger bars, a motorized dispensing unit, and fluid transfer lines from the IV bags to the motorized dispensing machine and from the motorized dispensing machine to a needle inserted into a patient in the hospital bed.
Figure 8:
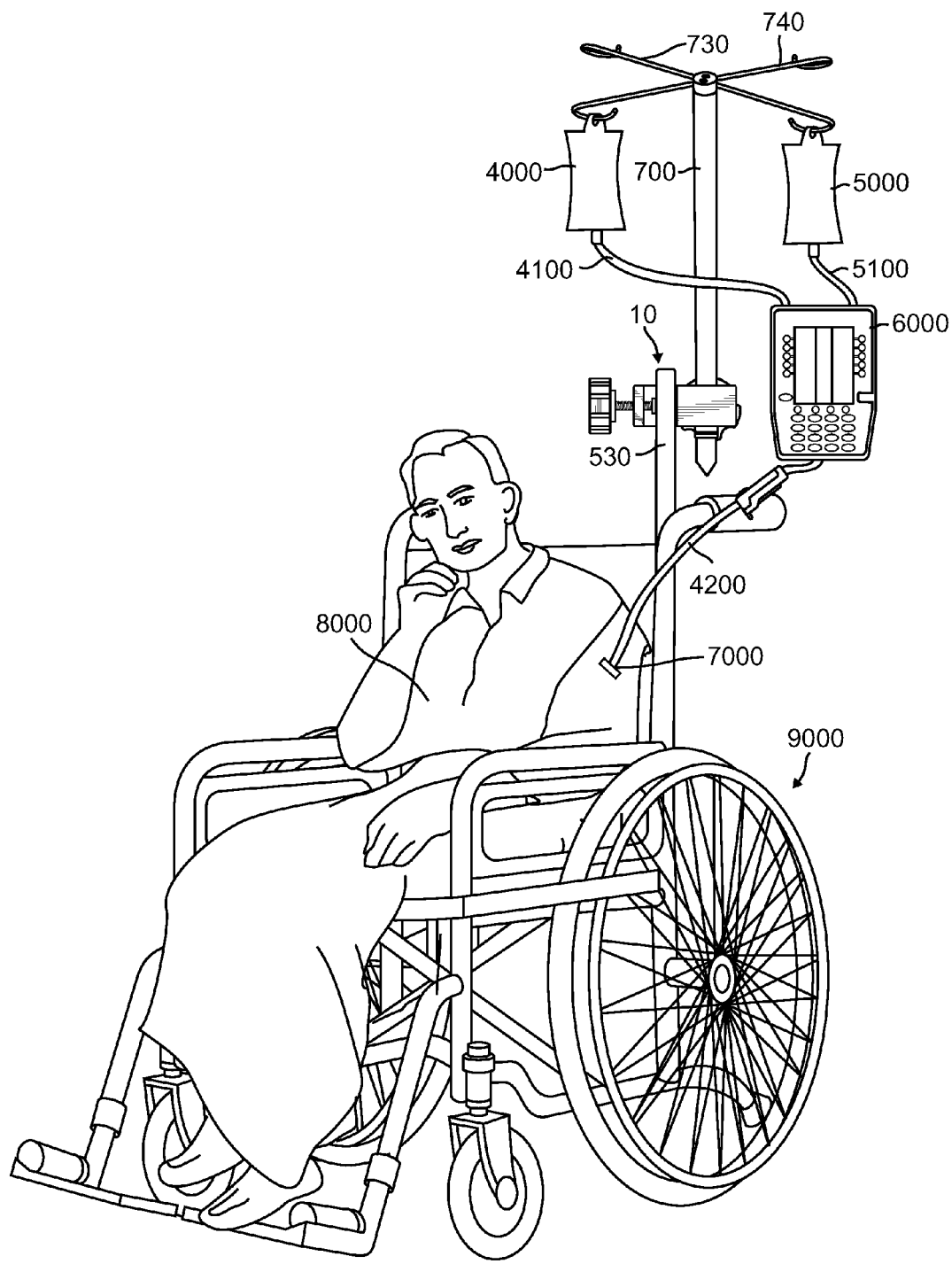
FIG. 8 is a perspective view of the present invention clamp apparatus clamped to pole of a wheelchair and retaining a short pole with IV medication bags retained on hanger bars, a motorized dispensing unit, and fluid transfer lines from the IV bags to the motorized dispensing machine and from the motorized dispensing machine to a needle inserted into a patient in the wheelchair.

The present invention is illustrated in operation in FIGS. 7 and 8.

FIG. 7 is a perspective view of the present invention clamp apparatus 10 clamped to pole 500 of a hospital bed 2000 and retaining a short pole 700 with the hanger bar innovation with IV medication bags 4000 and 5000 respectively retained on hanger bars 740 and 730, a motorized dispensing unit 6000, and fluid transfer lines 4100 and 5100 from the IV bags 4000 and 5000 to the motorized dispensing machine 6000 and from the motorized dispensing machine 6000 to a fluid transfer line 4200 to a needle 7000 inserted into a patient 8000 in the hospital bed 2000.

FIG. 8 is a perspective view of the present invention clamp apparatus 10 clamped to pole 550 of a wheelchair 9000 and retaining a short pole 700 with the hanger bar innovation with IV medication bags 4000 and 5000 retained on hanger bars 740 and 730, a motorized dispensing unit 6000, and fluid transfer lines 4100 and 5100 from the IV bags 4000 and 5000 to the motorized dispensing machine 6000 and from the motorized dispensing machine 6000 to a fluid dispensing line 4200 to a needle 7000 inserted into a patient 8000 in the wheelchair 9000.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A clamp used in conjunction with a first pole selected from the group consisting of a first pole integral with a hospital bed frame and an extended pole integral with a wheelchair, and also used in conjunction with an unsupported pole having a tubular pole section with a multiplicity of hanger bars retaining bags of medication with medication delivery members selected from the group consisting of fluid delivery lines in fluid communication with a respective bag at an end and in fluid communication with a medication delivery needle at an opposite end and a dispensing machine regulating respective dosages of mediation and receiving the fluid delivery lines in fluid communication at an end with a respective bag and in fluid communication at an opposite end with the dispensing machine and fluid delivery lines in fluid communication at one end with the dispensing machine and at an opposite end respectively in fluid communication with a medication delivery needle, the clamp comprising:

a. a body having a first section including a bent sidewall section and a longitudinal section, the bent sidewall section extending from an outer surface through a wall to an inner surface with an interior opening having a threaded sidewall with threads which extend from the outer surface to the inner surface, a first affixation member including a first rod with threads threadedly extending through the bent sidewall interior opening and engaged with threads of the bent sidewall interior opening, a retaining plate affixed at a proximal end of the first rod and a first closing knob affixed at a distal end of the first rod, the longitudinal section having an outer surface, a body and an inner surface, the first section terminating in an interior wall extending from the inner surface of the longitudinal section, the interior wall having a concave cavity aligned with the retaining plate of the first rod, the interior wall having a distal longitudinal section terminating in a free end, the first section including a pole retaining opening located between an interior surface of the concave cavity of the interior wall and the aligned retaining plate of the first rod to retain a first pole within the first section by a press fit retention created by rotation of the first closing knob to cause the retaining plate to press against the first pole to press fit retain the first pole between the retaining plate and the interior surface of the interior wall of the concave cavity, the location of the interior surface of the interior wall where the first pole is press fit retained identified as clamp point one;

b. a second section including a cylindrical member having an inner cylindrical chamber having an interior opening leading to the inner cylindrical chamber having an inner cylindrical surface and an exterior cylindrical surface, a proximal portion of an exterior surface of the cylindrical member extending to a spacer member which is integral with the cylindrical member, the spacer member extending from a proximal portion of the exterior cylindrical surface to a second longitudinal wall which is aligned with the longitudinal wall of first section, the spacer member having an interior opening having a sidewall with threads which extend from an outer surface of the spacer member to the surface of the inner cylindrical chamber, a second affixation member includes a second rod with threads threadedly extending through the interior opening of the spacer member and engaged with threads of the interior opening of the spacer member, a second closing knob is affixed at a distal end of the second rod, said unsupported pole insertable into the interior cylindrical chamber and retained within the interior cylindrical chamber by rotation of the second closing knob to cause an interior end of the second rod to press against said unsupported pole inserted into the cylindrical chamber, a location of the interior surface of the interior cylindrical chamber aligned with said clamp point one and is identified as clamp point two; and c. an intermediate spacer section formed between the first section and the second section by a first intermediate longitudinal wall integral with the longitudinal wall of the first section and the longitudinal wall of the second section and a second intermediate longitudinal wall integral with the extending wall of the interior wall of the first section and an exterior surface of the cylindrical member of the second section, the intermediate spacer member creating a spacer distance between said clamp point one and said clamp point two;

d. whereby the spacer distance enables a fisted hand grasping the unsupported pole to be positioned between said clamp point one and said clamp point two.

2. The clamp in accordance with claim 1, further comprising: the spacer distance is between 3/8 inch and 6 inches.

3. The clamp in accordance with claim 1, further comprising: the clamp is made of material selected from the group consisting of aluminum, steel and stainless steel.

4. An unsupported pole comprising:
a. a tapered bottom end to facilitate insertion of the unsupported pole into a cylindrical member of a clamp;
b. a first hanger bar and a second hanger bar with a notch in one of the hanger bars at a location where the first hanger bar and the second hanger bar intersect to enable the first hanger bar and the second hanger bar to be aligned with each other; and c. the first hanger bar positioned relative to the second hanger bar at an angle between 20 degrees and 60 degrees.

5. A clamp used in conjunction with a first pole integral with a frame of a patient accommodating apparatus and also used in conjunction with an unsupported pole having a tubular pole section with a multiplicity of hanger bars, the clamp comprising:

a. a body having a first section including a sidewall section extending from an outer surface through a wall to an inner surface with an interior opening having a threaded sidewall with threads which extend from the outer surface to the inner surface, a first affixation member including a first rod with threads threadedly extending through the sidewall section interior opening and engaged with threads of the sidewall section, a retaining plate affixed at a proximal end of the first rod and a first closing knob affixed at a distal end of the first rod, the first section terminating in an interior wall having a concave cavity aligned with the retaining plate of the first rod, the first section including a first pole retaining opening located between an interior surface of the concave cavity of the interior wall and the aligned retaining plate of the first rod to retain the first pole within the first section by a press fit retention created by rotation of the first closing knob to cause the retaining plate to press against the first pole to press fit retain the first pole between the retaining plate and the interior surface of the interior wall of the concave cavity, the location of the interior surface of the interior wall where the first pole is press fit retained identified as clamp point one;

b. a second section including a cylindrical member having an inner cylindrical chamber having an interior opening leading to the inner cylindrical chamber having an inner cylindrical surface and an exterior cylindrical surface, a proximal portion of an exterior surface of the cylindrical member extending to a spacer member which is integral with the cylindrical member, the spacer member extending from a proximal portion of the exterior cylindrical surface to a second longitudinal wall which is aligned with a first longitudinal wall of first section, the spacer member having an interior opening having a sidewall with threads which extend from an outer surface of the second spacer member to the surface of the inner cylindrical chamber, a second affixation member including a second rod with threads threadedly extending through the interior opening of the second spacer member and engaged with threads of the interior opening of the second spacer member, a second closing knob is affixed at a distal end of the second rod, an unsupported pole insertable into the interior cylindrical chamber and retained within the interior cylindrical chamber by rotation of the second closing knob to cause an interior end of the second rod to press against the unsupported pole inserted into the cylindrical chamber, a location of the interior surface of the interior cylindrical chamber aligned with said clamp point one and is identified as clamp point two; and c. an intermediate spacer section formed between the first section and the second section by a first intermediate longitudinal wall integral with the first longitudinal wall of the first section and the second longitudinal wall of the second section of the second spacer member and a second intermediate longitudinal wall integral with the extending wall of the interior wall of the first section and an exterior surface of the cylindrical member of the second section, the intermediate spacer section creating an intermediate spacer distance between said clamp point one and said clamp point two;

d. whereby the intermediate spacer distance enables a fisted hand grasping said unsupported pole to be positioned between said clamp point one and said clamp point two.

6. The clamp in accordance with claim 5, further comprising: the spacer distance is between ⅜ inch and 6 inches.

7. The clamp in accordance with claim 5, further comprising: the clamp is made of material selected from the group consisting of aluminum, steel and stainless steel.

* * * * *